United States Patent [19]

Connor et al.

[11] Patent Number: 5,188,769

[45] Date of Patent: Feb. 23, 1993

[54] PROCESS FOR REDUCING THE LEVELS OF FATTY ACID CONTAMINANTS IN POLYHYDROXY FATTY ACID AMIDE SURFACTANTS

[75] Inventors: Daniel S. Connor; Jeffrey J. Scheibel; Bruce P. Murch; Mark H. Mao; Eugene P. Gosselink; Roland G. Severson, Jr., all of Cincinnati, Ohio

[73] Assignee: The Procter & Gamble Company, Cincinnati, Ohio

[21] Appl. No.: 857,853

[22] Filed: Mar. 26, 1992

[51] Int. Cl.$^5$ .................. C07C 231/02; C07H 7/02; C11D 1/52; C11D 3/04

[52] U.S. Cl. ................ 252/548; 252/357; 252/529; 252/551; 536/53; 554/61; 554/65; 554/68

[58] Field of Search .............. 536/53; 554/61, 65, 554/68; 252/357, 529, 548, 551

[56] References Cited

U.S. PATENT DOCUMENTS

| | | | |
|---|---|---|---|
| 1,985,424 | 12/1934 | Piggott | 260/124 |
| 2,016,962 | 10/1935 | Flint | 260/127 |
| 2,429,445 | 10/1947 | Young | 252/548 |
| 2,653,932 | 9/1953 | Schwartz | 252/548 |
| 2,662,073 | 12/1953 | Meltretter | 252/548 |
| 2,703,798 | 3/1955 | Schwartz | 260/211 |
| 2,757,143 | 7/1956 | Katzman | 252/548 |
| 2,859,182 | 11/1958 | Carroll | 252/548 |
| 2,965,576 | 12/1960 | Wilson | 252/529 |
| 4,435,317 | 3/1984 | Gerritsen | 252/547 |

*Primary Examiner*—Dennis Albrecht
*Attorney, Agent, or Firm*—Jerry J. Yetter; Leonard W. Lewis

[57] ABSTRACT

The synthesis of polyhydroxy fatty acid amide surfactants exemplified by the compound $C_{11}H_{23}C(O)N(CH_3)CH_2[CHOH]_4CH_2OH$ by reacting a fatty acid ester with an N-alkyl sugar amine can result in contamination of the product surfactant by residual sources of fatty acids. These residual fatty acids may be unacceptable in high sudsing detergent compositions, such as dishwashing liquids, especially with Ca or Mg cations. The process of this invention reacts such contaminants with alkyl amines or, especially, ethanolamine, to convert them into fatty alkyl- or alkanolamides, which are quite acceptable in fully-formulated detergent compositions for home or industrial use.

12 Claims, No Drawings

PROCESS FOR REDUCING THE LEVELS OF FATTY ACID CONTAMINANTS IN POLYHYDROXY FATTY ACID AMIDE SURFACTANTS

FIELD OF THE INVENTION

The present invention relates to an improvement in a chemical reaction for preparing polyhydroxy fatty acid amide surfactants, whereby the content of undesirable fatty acid contaminants is reduced or substantially eliminated.

BACKGROUND OF THE INVENTION

The preparation of polyhydroxy fatty acid amide surfactants by the reaction of fatty esters with N-alkylamino polyols is of considerable commercial interest. However, the resulting N-alkylamido polyol reaction products, such as the fatty acid N-methyl glucamides, are often contaminated with residual nascent sources of fatty acids. Contamination by such materials may be tolerable if the user can afford to purify the polyhydroxy fatty acid amides prior to use. Or, as a possible alternative, the user presumably could arrange for special care to be taken during the reaction in order to minimize the levels of nascent sources of fatty acids. However, the manufacturer of high volume, low-cost chemicals such as detersive surfactants can ill-afford special handling techniques or materials which require expensive purification steps. For example, the manufacturer of high sudsing detergent compositions which contain polyhydroxy fatty acid amide surfactants (e.g., $C_8$-$C_{22}$ fatty acid amide derivatives of N-methyl glucamine or N-melhyl fructamine) requires an inexpensive source of such materials which have desirable low fatty acid levels, since such fatty acids (especially $C_{14}$, and higher chain lengths) can substantially reduce sudsing. Indeed, the manufacturer of high sudsing, high cleaning dishwashing liquids which are formulated to contain calcium and/or magnesium cations is also especially concerned with having a source of surfactants which contain little or no nascent fatty acids, due to the prospective formation of "curd" by the reaction of such cations with fatty acids which may contaminate the formulations.

The present invention solves the problem of contamination by nascent sources of fatty acids associated with the manufacture of polyhydroxy fatty acid amides, and thereby affords access to a high quality supply of this class of surfactants.

BACKGROUND ART

The following references are instructive: U.S. Pat. No. 1,985,424, issued Dec, 25, 1934; U.S. Pat. No. 2,016,962, issued Oct. 8, 1935; and U.S. Pat. No. 2,703,798, issued Mar. 8, 1955.

SUMMARY OF THE INVENTION

The present invention encompasses, in a process for preparing a primary reaction product comprising a polyhydroxy fatty acid amide surfactant, said reaction product containing undesirable amounts of free fatty acids or nascent sources of fatty acids, said process comprising a primary reaction between a polyhydroxy amine and a fatty acid ester, said primary reaction being carried out at a temperature below about 100.C so as to minimize formation of cyclized by-products in said reaction product, the improvement which comprises running the primary reaction under substantially water-free conditions, whereby the formation of free fatty acids and soaps is minimized and adding to said primary reaction product an amine reactant and subjecting said reaction product to a secondary reaction, whereby the total level of residual nascent and free fatty acid present in the product of the secondary reaction (i.e., in the final, overall product) is minimized, i.e., reduced to below about 1%, by weight, preferably below about 0.5%, by weight.

It is to be understood that by conducting the primary reaction under conditions which are substantially water-free, the formation of free fatty acids and soaps is minimized. Then, in the secondary reaction the residual nascent sources of fatty acid are minimized.

In a typical and preferred mode, said primary reaction product is prepared by a primary reaction of a $C_8$-$C_{22}$ fatty acid ester and a polyhydroxy amine, especially wherein the fatty acid ester is a methyl ester, and more especially wherein said primary reaction is carried out in the presence of a base catalyst. In a highly preferred mode, the primary reaction is carried out in a nonaqueous hydroxy solvent, especially methanol or 1,2-propanediol, or mixtures thereof, in the presence of an alkoxide catalyst, and in the absence of water.

A convenient process according to this invention is wherein said amine reactant used in the secondary reaction is a short chain ($C_1$-$C_4$) primary or (less preferred) secondary alkyl amine, or is a hydroxyalkyl amine, and especially wherein said amine reactant is a member selected from the group consisting of $C_1$-$C_3$ primary amines, and, more preferably, primary alkanolamines, and most preferably wherein said secondary reaction is carried out at a temperature of from about 50° C. to about 90° C., preferably 65°-85° C.

The invention herein thus provides an overall process for preparing high quality polyhydroxy fatty acid amide surfactants, comprising:

(a) a primary amidation reaction conducted under substantially water-free conditions between a fatty acid ester and a polyhydroxyamine, as illustrated by the reaction between $C_{10}$-$C_{18}$ fatty alkyl or alkenyl (especially oleyl) methyl esters and N-methyl glucamine in the presence of an alkoxide catalyst and a polyol and/or alcohol solvent, preferably at temperatures below about 100° C., as follows:

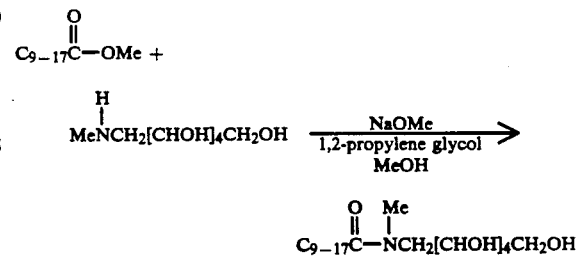

thereby providing the reaction product containing the polyhydroxy fatty acid amide surfactant which is substantially free of soaps and/or free fatty acids and substantially free of cyclized by-products, but which is contaminated with residual nascent fatty acids, followed by;

(b) a secondary reaction which comprises admixing with the contaminated reaction product of primary reaction (a) a primary alkanolamine, which reacts with said contaminants, whereby the level of residual source of nascent fatty acid is reduced to below about 0.5% in the final surfactant product.

A preferred process is wherein said alkanolamine reactant used in the secondary reaction is a member selected from the group consisting of monoethanolamine (most preferred) and 1-amino-2-propanol.

The invention also encompasses, in a process for preparing a detergent composition containing a source of calcium ions, magnesium ions, or mixtures thereof, said detergent composition comprising a polyhydroxy fatty acid amide surfactant which is prepared under substantially water-free conditions by reacting a fatty methyl ester reactant and a polyhydroxy amine to provide a polyhydroxy fatty acid amide surfactant reaction product which is undesirably contaminated with interfering amounts of residual sources of nascent fatty acid, the improvement which comprises employing the improved process disclosed above to prepare said polyhydroxy fatty acid amide surfactant which is substantially free of residual free or nascent fatty acid, whereby undesirable interactions between said calcium or magnesium ions and said residual fatty acid are minimized. In a preferred process, said detergent composition is in liquid form and contains at least about 0.10% by weight of added calcium or magnesium ion, or both, and less than about 1.0%, more preferably less than about 0.5%, by weight of fatty acid (i.e., either free fatty acid, soap or nascent fatty acid, or mixtures thereof).

All percentages, ratios and proportions herein are by weight, unless otherwise specified. The pressures specified herein are pounds per square inch gauge (psig).

DETAILED DESCRIPTION OF THE INVENTION

This invention provides an overall process for preparing high quality polyhydroxy fatty acid amide surfactants which are substantially free of contamination by residual sources of fatty acids. Since the process affords the desired surfactants using conventional, mainly renewable resources, the overall process will be described herein in some detail, although the improvement of this invention resides in the reduction of free fatty acids in the primary reaction by minimizing moisture content, and in the reduction of nascent fatty acid levels by means of the secondary reaction involving the amine and the undesired nascent source of fatty acid. Thus, the disclosure herein provides an overall commercial-type process, beginning with the formation of the polyhydroxy amine, followed by its conversion into the polyhydroxy fatty acid amide, followed by the reduction in residual nascent fatty acid levels using the technology afforded by the present invention.

As an overall proposition, the process described hereinafter will afford high quality N-alkylamino polyol reactants with desirable low Gardner Color and which are substantially free of nickel catalysts. Such N-alkylamino polyols can then be reacted with, preferably, fatty acid methyl esters to provide high yields (90-98%) of polyhydroxy fatty acid amides having desirable low levels (typically, less than about 0.1%) of cyclized by-products and also with improved color and improved color stability, e.g., Gardner Colors below about 4, preferably between 0 and 2. The content of nascent fatty acids present in the polyhydroxy fatty acid amide is minimized by the Secondary Reaction with amines, as disclosed herein. It will be understood that the nascent fatty acids are not thereby removed from the final product, but are converted into amido forms which can be tolerated in finished detergent compositions, even in liquid detergent compositions which contain calcium or magnesium cations. Indeed, by judicious selection of amines such as ethanolamine, the fatty acid monoethanolamides resulting from the secondary reaction herein are, themselves, desirable cleaning and suds-boosting ingredients, especially in liquid dishwashing detergents.

The following describes the reactants and reaction conditions for the overall process.

By "substantially water-free" or like terminology used herein is meant that all reactants, solvents, catalysts and apparatus are employed in as water-free state as is reasonably possible. Typically, solvents may be dried using molecular sieves; apparatus is swept dry with dry gas; reactants preferably contain the minimum possible amount of water. Typically, the moisture content of the reactants, solvents, etc., will be in the range of 0.2%, more preferably 0.1%, or less.

By "substantially free of nickel" herein is meant that the N-alkylamino polyol used in the primary reaction contains no more than about 20 parts per million (ppm) nickel, and preferably less than about 5 ppm nickel ($Ni++$). Nickel can be conveniently measured by conventional atomic absorption spectroscopy, using diluted samples (5/1 dilution to minimize interference).

By "reducible compounds" or "reducibles" herein is meant chemical compounds which contain reducing sugars either in their natural state or as an adduct with the amine such as N-methylglucamine. Such compounds include, but are not limited to, species such as glucose, fructose, maltose, xylose, N-methylglucosylamine, N-methylfructosylamine, N-methyl-N-glucosylglucamine. This is measured by g.c. analysis.

By "g.c. analysis" herein is meant gas-liquid chromatography ("g.l.c.") using Hewlett-Packard 5890 Series 2 on column injection using DB1 15 meter 0.25 $\mu$film thickness ID 250 $\mu$.

By "improved color" and/or "improved color stability" herein is meant the Gardner Color of the N-alkylamino polyol reactant used in the present process. Moreover, the Gardner Color of the fatty amide surfactants which are subsequently made therefrom is also substantially improved.

By "Gardner Color" herein is meant the standard Gardner measurement known in the art. A Gardner Color reading near zero (solution) represents a nearly colorless ("water-white") solution. Gardner Colors in the 4-7 range are only marginally acceptable for the N-alkylamino polyol reaction products, and it is preferred to achieve Gardner Colors below about 4, preferably 0 to about 2. Of course, use of sugars having low Gardner Colors (e.g., 0 or 1, i.e., water-white syrups) will help ensure that N-alkylamino polyols having desirably low Gardner Colors will be produced. Stated otherwise, use of low (0-2) Gardner Color sugars (preferably white solids or water-white solutions) and use of the reaction sequence disclosed herein results in low Gardner Color N-alkylamino polyols (white or slightly off-white solids).

By "improved odor" herein is meant that the odor character of the reaction product is substantially free of amine or "fish" type odor (once any excess N-alkylamine is removed) and also substantially free of typical browning sugar odors.

By "nickel catalyst" herein is meant any of the conventional Raney nickel or "supported" nickel catalysts well-known in the art. Conventional nickel under the trademark RANEY NICKEL 4200 (Grace Chemicals) is quite suitable for use herein. RANEY NICKEL 3200, (United Catalyst, Inc.) UCI: G-96B and G-49A and G-49C are also suitable. While not intending to be limited by theory, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pre-treated with pressurized hydrogen can be re-used in multiple subsequent reactions, thereby yielding a substantial overall cost savings.

By "pressurized hydrogen" or "hydrogen pressure" in the polyhydroxy amine-forming reaction herein is meant: for treatment of the nickel catalyst typically 500 psig –5,000 psig; for reaction of the N-alkylamine and sugar (steps c and d below), typically 200 psig–5,000 psig.

By "sugars" in the polyhydroxy amine-forming reaction herein is meant reducing sugars such as glucose, fructose, mannose, lactose, maltose, xylose and the like. The term "sugars" herein also includes glyceraldehyde. Such "sugars" include plant syrups such as cane syrups, corn syrups, potato starch-derived sugar syrups, hydrolyzed wood pulp-derived sugars and the like. High fructose, high glucose and high maltose syrups are economical and preferred, especially if their Gardner Color is satisfactory.

By "N-alkylamines" in the polyhydroxy amine-forming reaction herein is meant compounds such as the N-methyl, N-ethyl, N-propyl, etc., $C_1$-$C_{10}$ N-alkylamines, and the corresponding hydroxysubstituted amines, e.g., ethanolamine. The $C_1$-$C_3$ alkylamines are preferred, and N-methylamine is most preferred.

By "amine reactant" in the secondary reaction to reduce fatty acid levels herein is meant, as noted above, $C_1$-$C_4$ amines and alkanolamines, examples of which include monoethanolamine (preferred), propylamine, ethylamine, 3-amino-1,2-propanediol, 1-amino-2-propanol, 3-amino-1-propanol, tris-(hydroxymethyl)aminoethane, 2-amino-2-ethyl-1,3-propanediol, ammonia, and the like.

By "free fatty acids" herein is meant the fatty acids per se, or salts thereof, e.g., sodium salts, i.e., soaps.

By "residual nascent source of fatty acids" herein is meant, for example, unreacted fatty acid ester starting materials, complex ester-amides which unavoidably form in small amounts during the primary reaction, and any other potential source of free fatty acid. It will be appreciated by the chemical formulator that during the overall reaction, work-up and storage of the polyhydroxy fatty acid amide surfactants, such nascent sources of fatty acids can break down in the presence of water in even modestly basic or acidic conditions to release the undesired fatty acids.

By "cyclized by-products" herein is meant the undesirable reaction by-products of the primary reaction wherein it appears that the multiple hydroxyl groups in the polyhydroxy fatty acid amides can form ring structures which are, in the main, not readily biodegradable. It will be appreciated by those skilled in the chemical arts that the preparation of the polyhydroxy fatty acid amides herein using the di- and higher saccharides such as maltose will result in the formation of polyhydroxy fatty acid amides wherein linear substituent Z (which contains multiple hydroxy substituents and which is more fully defined hereinafter) is naturally "capped" by a polyhydroxy ring structure. Such materials are not cyclized by-products, as defined herein.

Formation of N-Alkylamino Polyol Raw Material

The preparation of the N-alkylaminol polyols used in the present process can be conducted in any well-stirred pressure vessel suitable for conducting hydrogenation reactions. In a convenient mode, a pressure reactor with a separate storage reservoir is employed. The reservoir (which, itself, can be pressurized) communicates with the reactor via suitable pipes, or the like. In use, a stirred slurry of the nickel catalyst is first treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment preferred.) After removal of excess slurry medium (water) the N-alkyl amine is introduced into the reactor. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for reducibles using gas chromatography ("g.c."), or by heating the sample to about 100° C. for 30-60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

In more detail, the process for preparing N-alkylamino polyols by reacting an N-alkylamine with a reducing sugar in the presence of a nickel catalyst under hydrogen pressure preferably will comprise:

(a) removing substantially all oxides of nickel from the nickel catalyst (conveniently, this can be done by contacting the nickel catalyst with hydrogen, typically under pressure and temperature of 50°–185° C. at 500–1,500 psig hydrogen);

(b) admixing the nickel catalyst from (a) with the N-alkylamine to provide mixture (b) under hydrogen pressure prior to admixture with the sugar;

(c) admixing the sugar with mixture (b) under hydrogen pressure;

(d) conducting the reaction of the sugar with the N-alkyl amine/nickel catalyst mixture (b) at a temperature below about 80° C. and under hydrogen pressure (typically at least 250 psig, preferably at least 500 psig) until at least about 95% by weight of the reducible compounds are no longer present in the reaction mixture;

(e) continuing the reaction, optionally at a temperature of up to about 120° C., until at least about 99.9% by weight of the reducible compounds are no longer present in the reaction mixture; and (f) recovering the N-alkylamino polyol, preferably without purification.

A typical process is wherein the nickel catalyst level is in the range of from about 5% to about 50%, most typically about 10% to about 30%, by weight of the sugar reactants, for optimal throughput. Preferably step (d) of the process is carried out at a temperature of from about 40° C. to about 70° C. Step (e) is preferably carried out at a temperature from about 80° C. to about 20° C. The catalyst may be used in repeat batches, as is.

The above process thus affords a convenient reaction for the preparation of compounds which include, but are not limited to, N-alkyl glucamine, N-alkyl fructamine, N-alkyl maltamine or N-alkyl glycerol amine, comprising the steps of:

(a) admixing a nickel catalyst which is substantially free of oxides of nickel with an N-alkylamine (preferably N-methylamine);

(b) under hydrogen pressure, admixing an aqueous solution of glucose, fructose, maltose or glyceraldehyde, respectively, with the mixture from step (a);

(c) allowing the mixture from step (b) to react at a temperature of from about 40° C. to about 70° C. until at least about 95% by weight of the reducible compounds are no longer present in the reaction mixture; and (d) allowing the reaction from step (c) to continue at a temperature below about 120° C. until at least about 99.9% by weight of the reducible compounds are no longer present in the reaction mixture.

Preferably the process is conducted with said catalyst being present at the 10% to 30% level relative to sugar.

When preparing 1,2-propanediol derivatives (e.g., N-alkyl glycerol amines) the formulator may elect to react an N-alkylamine with, for example, 3-chloro-1,2-propanediol or glycidol, at room temperature to about 65° C., typically in ethanol or water.

Primary Reaction to Form Polyhydroxy Fatty Acid Amides

The primary reaction herein for preparing polyhydroxy fatty acid amide surfactants, comprises reacting a member selected from the group consisting of, preferably, fatty acid esters with an N-alkylamino polyol. In a preferred process, the fatty acid ester is a $C_{10}$–$C_{18}$ a alkyl or alkenyl fatty acid methyl ester and the N-alkylamino polyol is selected from N-methyl glucamine, N-methyl fructamine, N-methyl maltamine and N-methyl glycerol amine.

The amide-forming primary reaction herein can be illustrated by the formation of N-lauroyl N-methyl glucamine, as follows.

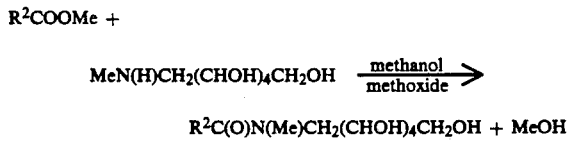

$R^2COOMe +$ $MeN(H)CH_2(CHOH)_4CH_2OH \xrightarrow{\text{methanol}}{\text{methoxide}}$ $R^2C(O)N(Me)CH_2(CHOH)_4CH_2OH + MeOH$ wherein $R^2$ is $C_{11}H_{22}$ alkyl.

More generally, the process herein can be used to prepare polyhydroxy fatty acid amide surfactants of the formula:

$$\begin{matrix} & O & R^1 \\ & \| & | \\ R^2 - & C - & N - Z \end{matrix} \quad (I)$$

wherein: $R^1$ is H, $C_1$–$C_4$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of $-CH_2-(CHOH)_{n-1}-CH_2OH$, $-CH(CH_2OH)-(CHOH)_{n-1}-CH_2OH$, $-CH_2-(CHOH)_2(CHOR')-(CHOH)-CH_2OH$, where n is an integer from 1 to 5, inclusive, and R' is H or a cyclic mono- or poly- saccharide, and alkoxylated derivatives thereof. Most preferred are glycityls wherein n is 4, particularly $-CH_2-(CHOH)_4-CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl.

$R^2$-CO-N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, 2,3-dihydroxypropyl (from glyceraldehyde), etc.

The following reactants, catalysts and solvents can conveniently be used herein, and are listed only by way of exemplification and not by way of limitation.

Reactants - As noted above, various fatty ester reactants can be used herein, but fatty methyl esters are most preferred. Various other fatty esters can be used in the primary reaction, including mono-, di- and tri-esters (i.e., triglycerides). Methyl esters are convenient and commercially available with low Gardner Color, and ethyl esters, and the like are all quite suitable. The polyhydroxyamine reactants include N-alkyl and N-hydroxyalkyl polyhydroxyamines with the N-substituent group such as $CH_3-$, $C_2H_5-$, $C_3H_7-$, $HOCH_2CH_2-$, and the like. As noted above, such materials preferably are substantially free of nickel catalysts. Mixtures of the ester and mixtures of the polyhydroxyamine reactants can also be used.

Catalysts - The catalysts used in the primary reaction are basic materials such as the alkoxides (preferred), hydroxides - if provision is made to remove water from it and polyhydroxyamine prior to addition of ester - carbonates, and the like. Preferred alkoxide catalysts include the alkali metal $C_1$–$C_4$ alkoxides such as sodium methoxide, potassium ethoxide, and the like. The catalysts can be prepared separately from the reaction mixture, or can be generated future using an alkali metal such as sodium. For in situ generation, e.g., sodium metal in the methanol solvent, it is preferred that the other reactants not be present until catalyst generation is complete. The catalyst typically is used at 0.1-10, preferably 0.5-5, most preferably 5 mole percent of the ester reactant. Mixtures of catalysts can also be used.

- Solvents - The organic hydroxy solvents used in the primary reaction include methanol, ethanol, glycerol, 1,2-propanediol, 1,3-propylene glycol, and the like. Methanol is a preferred alcohol solvent and 1,2-propanediol (propylene glycol) is a preferred diol solvent. Mixtures of solvents can also be used.

General Reaction Conditions - As noted, it is desired to prepare the products of the primary reaction (amidation) while minimizing the formation of cyclized by-products, ester amides and color bodies. Reaction temperatures below about 135° C., typically in the range of from about 40° C. to about 100° C., preferably 60° C. to 90° C., are used to achieve this objective, especially in batch processes where reaction times are typically on the order of about 90 minutes, or even up to 3 hours. Most preferably, this reaction is conducted at 85° C. Somewhat higher temperatures can be tolerated in continuous processes, where residence times can be shorter. All reactants, catalysts, solvents, etc. should be substantially dry. For example, the fatty esters and N-methyl glucamine preferably contain less than about 0.1% water. The concentration ranges of the reactants and solvent provide for example, what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels. However, at the higher concentrations the reaction systems are somewhat more difficult to work with, and require more efficient stirring (due to their thickness), and the like, at least in the early stages of the reaction. However, once the reaction proceeds to any appreciable extent, the viscosity of the reaction system decreases and ease of mixing increases. In one mode, product yields can be increased a few percent by allowing the reaction mixture to "age" (even to solidify) a few hours or days to allow final traces of starting materials to react at lower temperatures.

EXAMPLE I

Preparation of Polyhydroxyamine Reactant

Catalyst Treatment - Approximately 300 mls of RANEY NICKEL 4200 (Grace Chemicals) is washed with deionized water (1 liter total volume; 3 washings) and decanted. The total catalyst solids can be determined by the volume-weight equation provided by Grace Chemicals, i.e., [(total wt. catalyst+water)-- (water wt. for volume)]×7/6=Nickel solids.

308.21 g. of the catalyst Ni solids basis are loaded into a 2 gallon reactor (316 stainless steel baffled autoclave with DISPERSIMAX hollow shaft multi-blade impeller from Autoclave Engineers) with 4 liters of water. The reactor is heated to 130° C. at 1400-1600 psig hydrogen for 50 minutes. The mixture is cooled to room temperature at 1500 psig hydrogen and left overnight. The water is then removed to 10% of the reactor volume using an internal dip tube.

Reaction - The reactants are as follows. 881.82 mls. 50% aqueous monomethylamine (Air Products, Inc.; Lot 060-889-09); 2727.3 g. 55% glucose syrup (Cargill; 71% glucose; 99 dextrose equivalents; Lot 99M501).

The reactor containing the $H_2O$ and Raney nickel prepared as noted above is cooled to room temperature and ice cold monomelhylamine is loaded into the reactor at ambient pressure with $H_2$ blanket. The reactor is pressurized to 1000 psig hydrogen and heated to 50° C. for several minutes. Stirring is maintained to assure absorption of $H_2$ in solution.

The glucose is maintained in a separate reservoir which is in closed communication with the reactor. The reservoir is pressurized to 4000 psig with hydrogen. The glucose (aqueous solution) is then transferred into the reactor under $H_2$ pressure over time. (This transfer can be monitored by the pressure change in the reservoir resulting from the decrease in volume of the sugar solution as it is transferred from the reservoir into the main reactor. The sugar can be transferred at various rates, but a transfer rate of ca.100 psig pressure drop per minute is convenient and requires about 20 minutes for the volume used in this run.) An exotherm occurs when the aqueous sugar solution is introduced into the reactor; the 50° C. internal temperature raises to ca. 53° C.

Once all the glucose has been transferred to the reactor the temperature is maintained at 50° C. for 30 minutes. Hydrogen uptake is monitored by a pressure gauge. Stirring is continued throughout at 800-1,100 rpm or greater.

The temperature of the reactor is increased to 60° C. for 40 minutes, then to 85° C. for 10 minutes, then to 100° C. for 10 minutes. The reactor is then cooled to room temperature and maintained under pressure overnight. The reaction product dissolved in the aqueous reaction medium is conveniently recovered by using an internal dip tube with hydrogen pressure. Particulate nickel can be removed by filtration. Preferably, an internal filter is used to avoid exposure to air, which can cause nickel dissolution. Solid N-methyl glucamine is recovered from the reaction product by evaporation of water.

The foregoing procedure can be repeated using fructose as the sugar to prepare N-methyl fructamines.

The foregoing procedure can also be repeated using glyceraldehyde as the sugar to prepare N-methyl glycerol amine (3-methylamino-1,2-propanediol).

Conversion of Polyhydroxy Amine to Polyhydroxy Fatty Acid

Amide Surfactant Reaction Product and Minimization of

Nascent Fatty Acids by the Secondary Reaction

As the initial step, the substantially water-free N-methyl glucamine prepared above is reacted with fatty acid methyl esters to prepare the corresponding fatty acid amides of N-methyl glucamine in the manner disclosed above and in the experimental details, hereinafter. It will be appreciated that coconut fatty acid methyl esters, palm oil fatty acid esters, tallow fatty acid esters, oleyl esters, polyunsaturated fatty acid esters, and the like, can all be used in this reaction, and various N-alkyl polyols, e.g., N-methyl fructamine, N-methyl maltamine, etc., can be used in place of the N-methyl glucamine.

The secondary reaction can thereafter be carried out using primary alkyl amines and alkanolamines. However, it will be appreciated by the chemist that, since alkyl amines generally have undesirable odors, as compared with alkanolamines, it is preferred to employ the alkanolamines. By so doing, removal of traces of unreacted amine material from the final product of the process is unnecessary, since products with improved odor are secured.

Moreover, while secondary amines will function adequately in the process herein to remove the nascent sources of fatty acids, such amines can undesirably form nitrosamines. Accordingly, the primary amines, especially the primary alkanolamines such as ethanolamine ("mono-ethanolamine") are much preferred for use in the secondary reaction herein.

It will be further appreciated that it is desirable that the secondary reaction herein be carried out quickly, such that decomposition of the desired polyhydroxy fatty acid amide surfactant is kept to a minimum. In essence, the secondary reaction is an amidation reaction, and seems to be potentiated and accelerated by having a solvent supportive of nucleophilic reaction present. Since methanol is such a solvent, and is also one of the preferred solvents for use in the primary reaction herein, it suffices quite well to also act as the solvent for the secondary reaction. Preferably, at least about 6-8% by weight of such solvent which is supportive of nucleophilic reactions, especially methanol, is used in the secondary reaction of this invention, as well as some 1,2-propanediol. 1,2-propanediol, alone, can also serve as the solvent for the secondary reaction, but does not appear to be quite as effective as when methanol is present. Other lower alcohols, such as ethanol and isopropanol, could also be used, but may be poorer choices than methanol or mixtures of methanol/1,2-propanediol. Under such circumstances, some minimal loss (ca. about a 1% decrease in overall yield) of polyhydroxy fatty acid amide surfactant may be unavoidable, but this is usually an acceptable trade-off for the desired decrease in fatty acids in the final product.

The reaction temperature for the secondary reaction should preferably be about 85° C., or below, typically in the 65° C.-85° C. range. It will be appreciated that use of excessively high temperatures may desirably speed the secondary reaction, but will undesirably begin to cause cyclization of the polyhydroxy fatty acid amides. While temperatures up to about 120° C. might be tolerable for short periods of time, it would, of course, be undesirable to decrease nascent fatty acid content at the expense of increasing the level of cyclized by-product. The following further illustrates the Primary Reaction followed by the Secondary Reaction.

Apparatus: 500 ml three necked flask, paddle stirrer, reflux condenser with drying tube, thermometer reaching into reaction and a gas inlet tube. The flask is heated with a thermostatted oil bath.

Primary Reaction

The apparatus is predried under nitrogen sweep, cooled and the sweep is shut off. A tare weight is taken without the condenser. Pure powdered N-methylglucamine ("NMG") 97.5 g (0.5 mole), 107 g (0.5 mole) 95% methyl dodecanoate and 18.9 g propylene glycol (solvent) are placed into the flask; the moisture content of each reactant is, respectively, 0.3% and 0.1%, and the solvent is dried over molecular sieves. The mixture is heated to 68° C. with stirring to give a viscous paste; 5.4 g (0.025 mole) 25% sodium methoxide in methanol is then added. The time is taken as zero, and the reaction then brought quickly to 85° C., and held at 85° C. with continuous stirring, no vacuum, no nitrogen sweep. Within 5 minutes a thin milky suspension is formed which clears to a homogeneous clear low viscosity liquid at 55 minutes. During this reaction no reflux is observed, although methanol evolution is calculated to reach 9.1% at complete amidation with NMG. At 150 minutes, the weight of the reaction is within 2 g of initial; a small sample is taken.

Secondary Reaction

Immediately following the Primary Reaction, 7.6 g (0.125 mole) of dry ethanolamine is added. Vacuum/nitrogen sweep is then applied as stirring and temperature are maintained. At the 210 minute point the vacuum reaches 11 psi (4 psi absolute). Weighing indicates about 1.5 to 2% of reaction weight in excess of theoretical removal of all methanol from catalyst and ester. The resulting product has the following analysis and is suitable for use in high sudsing detergent compositions.

| | GC Area % | Calculated Concentrations |
|---|---|---|
| Methyl ester | 0.1% | 0.1% |
| Fatty acid/soap | 0.3% | 0.2% |
| NMG | 6.5% | 5.5% |
| Monoethanol amide | 2.6% | 2.2% |
| Total glucoseamide | 89.9% | 76.4% |
| $C_{10}$ | 1.1% | 0.9% |
| $C_{12}$ | 87.6% | 74.5% |
| $C_{14}$ | 1.2% | 1.0% |
| Ester amide | 0.1% | 0.1% |
| Assumed components not observed in GC | | |
| Propylene glycol | | 10.0% |
| Methanol | | 2.0% |
| Monoethanolamine | | 3.0 |
| TOTAL | | 99.5% |

The following is intended to illustrate the use of the polyhydroxy fatty acid amide surfactants made in accordance with this invention in finished liquid detergent compositions, but is not intended to be limiting thereof. Solid compositions can be prepared by replacing the fluid carrier (e.g., water) in such compositions with a water-soluble solid carrier such as sodium sulfate. Preferred liquid compositions will contain at least about 0.10%, preferably at least about 0.5%, by weight of calcium or magnesium ions, or both. Stated otherwise, the amount (molar ratio) of calcium or magnesium is typically $0.1\times$ to $2.0\times$ that of the anionic (e.g., sulfated or sulfonated) surfactant in such compositions.

EXAMPLE II

The following Examples illustrate light duty liquid detergent compositions which are especially adapted for dishwashing and other hard surface cleaning operations. In the Examples A-D, the surfactants comprise various alkyl ethoxy sulfate surfactants which, using standard terminology, are abbreviated to indicate their average degree of ethoxylation; thus $C_{12-13}EO(0.8)$ sulfate indicates a sulfated mixed $C_{12}$-$C_{13}$ alcohol fraction having an average degree of ethoxylation of 0.8. These anionic ethoxy sulfates are preferably used in their Na+ or NH$_4$30 salt form. The $C_{12-13}$ amine oxide is a mixed $C_{12-13}$ (average) dimethyl amine oxide. The $C_{12-14}$ AP betaine is $C_{12/14}H_{25/29}CONH(CH_2)_3N+(CH_3)_2$-$CH_2CO_2H$. The $C_{12-14}$ AP sultaine is $C_{12}/C_{14}H_{25/29}CONH(CH_2)_3N+$-$(CH_3)_2CH_2CH(OH)CH_2SO_3H$. The $C_{12-14}$ DM betaine is $C_{12/14}H_{25/29}N+$-$(CH_3)_2CH_2CO_2H$. The ethoxylated nonionic surfactant designated $C_{9-1}EO(8)$ refers to $C_9-C_{11}$ alcohols ethoxylated with an average of 8 moles of ethylene oxide, respectively. The Ca++ and Mg++ cations are conveniently introduced into the compositions as $CaCl_2$ and $MgCl_2$. The balance of the compositions comprises water and citrate/propylene glycol present in the glucamide surfactant (1-5%) and 1-3% cumene sulfonate or xylene sulfonate hydrotrope. The pH is typically 6.8-7.4 ($NH_4+$ salts) or 7-8.2 (Na+ salts).

| Ingredient | Percent (wt.) | | | |
|---|---|---|---|---|
| | A | B | C | D |
| $C_{12-14}$ N-methyl glucamide | 11 | 8 | 12.7 | 9 |
| $C_{12-13}$ EO (0.8) sulfate | — | 16 | 10.0 | 9 |
| $C_{12-14}$ EO (3) sulfate | 11 | — | 2.7 | 14 |
| $C_{12-13}$ EO (6.5) sulfate | — | — | — | 3 |
| $C_{12-14}$ AP betaine | — | — | 2 | — |
| $C_{12-14}$ AP sultaine | — | — | — | 1.0 |
| $C_{12-13}$ amine oxide | 2.5 | — | — | 1.0 |
| $C_{12-14}$ DM betaine | — | 2.0 | — | — |
| $C_{9-1}$ EO (8) | 0.5 | 8 | 7 | — |
| Ca++ | — | — | 0.5 | 1.0 |
| Mg++ | 0.9 | 0.25 | — | — |
| Balance | Bal | Bal | Bal | Bal |

EXAMPLE III

| Ingredients | Percent (wt.) | | | |
|---|---|---|---|---|
| | A | B | C | D |
| $C_{12-14}$ alkyl ethoxy sulfate (1 EO) | 16 | 9 | 12 | — |
| $C_{12-14}$ alkyl ethoxy sulfate (3 EO) | — | 14 | — | 11 |
| $C_{10}$ alkyl ethoxylate (8 EO) | 7 | 3 | 7 | 1 |
| $C_{12-14}$ N-methyl glucamide | 8 | 9 | 12 | 6 |
| Coconut diethanolamide | — | — | — | 5 |
| Dimethyl dodecyl amine oxide | — | 1 | — | 2 |
| Cocoamidopropyl hydroxysultaine | — | 1 | 3 | — |
| Cocoamidopropyl betaine | 2 | — | — | — |
| $Mg^{2+}$ | — | — | 1 | 1 |
| $Ca^{2+}$ | 0.5 | 1 | — | — |
| Sodium toluene sulfonate | 3 | 3 | 3 | 3 |
| Ethanol | 4 | 4 | 4 | 4 |
| Water | Balance | | | |

The foregoing liquid compositions which contain only the source of calcium ions will most preferably comprise less than about 0.1% by weight of residual fatty acids or nascent fatty acids. In yet another embodiment, liquid detergent compositions can contain sources of both calcium ions and magnesium ions; under such circumstances the final compositions will preferably contain less than about 0.3% by weight of residual fatty acids or nascent fatty acids.

It will be further appreciated that the present invention encompasses not only the processes disclosed herein, but also the products made thereby, especially the polyhydroxy fatty acid amide surfactants substantially free of cyclized by-products, free fatty acids and nascent fatty acids made by the process herein.

What is claimed is:

1. In a process for preparing a primary reaction product comprising a polyhydroxy fatty acid amide surfactant, said reaction product containing undesirable amounts of free fatty acids or nascent source of fatty acids, said process comprising a primary reaction between a sugar-derived or glyceraldehyde-derived polyhydroxy amine and a fatty acid ester, said primary reaction being carried out at a temperature below about 100° C. so as to minimize formation of cyclized by-products in said reaction product, the improvement which comprises running the primary reaction under substantially water-free conditions, whereby the formation of free fatty acids and soaps is minimized, and adding to said primary reaction product an amine reaction which is a member selected from the group consisting of ammonia, short-chain alkyl amines and short-chain hydroxyalkyl amines and subjecting said reaction product to a secondary reaction, whereby the total level of residual nascent and free fatty acid present in said primary reaction product is reduced to below about 1%, by weight.

2. A process according to claim 1, wherein said primary reaction product is prepared by a primary reaction of a $C_8-C_{22}$ fatty acid ester and a polyhydroxy amine.

3. A process according to claim 2, wherein the fatty acid ester is a methyl ester, and said primary reaction is carried out in the presence of a base catalyst.

4. A process according to claim 3, wherein the primary reaction is carried out in a hydroxy solvent in the presence of an alkoxide catalyst.

5. A process according to claim 1, wherein the amine reaction in said secondary reaction is a $C_1-C_4$ primary alkyl amine or $C_1-C_4$ primary hydroxyalkyl amine.

6. A process according to claim 5, wherein said amine reactant used in said secondary reaction is monoethanolamine, and wherein said secondary reaction is carried out at a temperature of from about 50° C. to about 90° C.

7. An improved process for preparing polyhydroxy fatty acid amide surfactants comprising:
 (a) a primary amidation reaction conducted under substantially water-free conditions between a fatty acid ester and a sugar-derived or glyceraldehyde-derived polyhydroxyamine to prepare a polyhydroxy fatty acid amide surfactant which is contaminated with residual nascent fatty acids, followed by;
 (b) a secondary reaction which comprises admixing and reacting with the reaction product of primary reaction (a) an amine reactant which is a member selected from the group consisting of ammonia, short-chain alkyl amines and short-chain hydroxy alkly amines, whereby the level of residual nascent fatty acids and free fatty acids is lowered to below about 0.5% by weight in the final surfactant.

8. A process according to claim 7 wherein said amine reactant is a member selected from the group consisting of monoethanolamine and 1-amino-2-propanol.

9. In a process for preparing a detergent composition containing a source of calcium ions, magnesium ions, or mixtures thereof, said detergent composition comprising a polyhydroxy fatty acid amide surfactant which is prepared by reacting a fatty acid ester and a sugar-derived or glyceraldehyde-derived polyhydroxy amine to provide a polyhydroxy fatty acid amide surfactant reaction product which is undersirably contaminated with interfering amounts of residual fatty acids or nascent fatty acids, the improvement which comprises adding to said detergent composition the polyhydroxy fatty acid amide surfactant prepared according to claim 1 which is substantially free of said residual fatty acids or nascent fatty acids, whereby undesirable interactions between said calcium or magnesium ions and said residual fatty acid are minimized.

10. A process according to claim 9 wherein said detergent composition is in liquid form and contains at least about 0.10% by weight of added calcium ion, magnesium ions, or mixtures thereof and less than about 1.0% by weight of residual fatty acid or nascent fatty acids.

11. A process according to claim 10 wherein said liquid detergent composition contains a source of calcium and magnesium ions and comprises less than about 0.3% by weight of residual fatty acids or nascent fatty acids.

12. A process according to claim 10 wherein said liquid detergent composition contains a source of calcium ions and comprises less than about 0.1% by weight of residual fatty acids or nascent fatty acids.

* * * * *

UNITED STATES PATENT AND TRADEMARK OFFICE
CERTIFICATE OF CORRECTION

PATENT NO. : 5,188,769
DATED : February 23, 1993
INVENTOR(S) : D. S. Connor et al It is certified that error appears in the above-identified patent and that said Letters Patent is hereby corrected as shown below:

Column 1, line 34, "N-melhyl" should be --N-methyl--.

Column 2, line 59, "$C_{9-17}C$" should be --$C_{9-17}$ C--.

Column 4, line 40, "0.25 µfilm" should be --0.25 µ film--.

Column 7, line 56, "$C_{11}H_{22}$" should be --$C_{11}H_{23}$--.

Column 8, line 65, "future" should be --*in situ*--.

Column 12, line 61, "$NH_430$" should be --$NH_4^+$--.

Signed and Sealed this

Nineteenth Day of April, 1994

Attest:

*Attesting Officer*

BRUCE LEHMAN
*Commissioner of Patents and Trademarks*